United States Patent [19]

Sasaki et al.

[11] 4,407,843
[45] Oct. 4, 1983

[54] SMEAR SAMPLE PREPARING METHOD

[76] Inventors: Susumu Sasaki, 2-75, Shoei-cho, Mizuho-ku, Nagoya-shi, Aichi-ken; Tomohiko Sakaki, 2-60, Ikesono-cho, Chikusa-ku, Nagoya-shi, Aichi-ken, both of Japan

[21] Appl. No.: 295,083

[22] Filed: Aug. 21, 1981

Related U.S. Application Data

[63] Continuation of Ser. No. 92,282, Nov. 8, 1979, abandoned, which is a continuation of Ser. No. 891,766, Mar. 30, 1978, abandoned.

[30] Foreign Application Priority Data

Mar. 31, 1977 [JP] Japan ................................ 52-36536

[51] Int. Cl.³ ........................................... B05C 11/04
[52] U.S. Cl. ...................................... 427/2; 118/100; 118/401
[58] Field of Search ............... 118/100, 120, 238, 506, 118/241, 696, 706, 242, 401; 427/2, 4

[56] References Cited

U.S. PATENT DOCUMENTS

| | | | |
|---|---|---|---|
| 2,687,111 | 8/1954 | Deniston | 118/241 X |
| 3,683,850 | 8/1972 | Grabhorn | 118/100 |
| 3,756,196 | 9/1973 | Furuuchi et al. | 118/401 |
| 3,880,111 | 4/1975 | Levine et al. | 118/100 X |
| 3,888,206 | 6/1975 | Faulkner | 118/100 |
| 3,961,599 | 6/1976 | Jones, Jr. | 118/410 X |
| 4,061,108 | 12/1977 | Levine et al. | 118/120 X |
| 4,096,824 | 6/1978 | Levine et al. | 118/100 |

FOREIGN PATENT DOCUMENTS 439124  1/1927  Fed. Rep. of Germany ...... 118/120

*Primary Examiner*—John P. McIntosh
*Attorney, Agent, or Firm*—Browdy & Neimark

[57] ABSTRACT

An apparatus for spreading a smear over a slide with a spreader (slide) for microscopic observation, includes a mechanism for suitably varying the relative spreading speed between the slide and the spreader, and/or the spreading angle formed between the slide and the spreader, in order to maintain the thickness of the smear at a constant value, by means of imparting a programmatic command to vary the speed and/or the angle, with the aid of a servomotor and/or a cam means.

6 Claims, 9 Drawing Figures

SMEAR SAMPLE PREPARING METHOD

This is a continuation of parent, copending application Ser. No. 92,282, filed Nov. 8, 1979 now abandoned, itself a continuation of application Ser. No. 891,766, filed Mar. 30, 1978, now abandoned.

FIELD OF THE INVENTION

The present invention relates to a smeared specimen (or smear sample, hereinafter simply called smear) preparing method which is used, for example, in microscopic observation, and an apparatus for desirably spreading a subject matter (practically non-free-flow fluid, such as blood) over a plane surface such as a slide. More particularly, the present invention relates to spreading (smearing) a subject matter in a desired uniform thickness over the slide and an apparatus therefor.

BACKGROUND OF THE INVENTION

For the purpose of simplifying the explanation, a smearing or spreading method of subject blood over a slide for microscopic observation (examination) used for medical diagnoses will be taken as an example. Obviously, subject matter other than blood may be spread according to the present invention.

As will later be described, referring to the drawings, conventionally known arts of smearing a subject blood over a slide are all disadvantageous or faulty in that the smears prepared are of non-uniform thickness according to the location and have a non-uniform distribution of cells.

As representative of the prior art, the Lecture on Clinical Examination Vol. 15, Haematology, by Shiro Hino published in 1972 from the ISHIYAKU SHUPPAN (Medical and Dental Pharmaceutics Publishing Co. Ltd.) will be partly cited, referring to pages 134–149. Besides, the following two books should be referred to as influential writings in this field: (1) Hematology for Medical Technologist, 3rd Edition, by SEIBERD, C. E., published by LEE AND FEBIGER in 1964, pages 219–251. (2) Clinical Hematology, 6th Edition, by WINTROBE, M. H., published by LEE AND FEBIGER in 1967, pages 444–447.

In one method, a technician holds a slide horizontally in one of his hands on which is placed a drop of subject blood, near one end of the slide, and a spreader slide (hereinafter simply called spreader) in the other hand so as to touch the first slide on the subject blood with the inner lower surface of the spreader at the lower end thereof selecting a certain acute angle within the range of 20–40 degrees. The drop of the subject blood positioned in a wedge-shaped space formed between the slide and the spreader contact both by capillary action, and spreads as a film over the slide surface as a film, as the spreader is moved horizontally at a certain constant speed, with the one end thereof being kept in touch with the slide surface and the contact angle kept unchanged.

Such a smear of blood is to be examined under a microscope, after fixing and staining, for providing necessary data for medical diagnoses based on, e.g., kind, type, or number of blood cells. The above-mentioned method of smear preparing is faulty for this purpose in that the thickness of the smear is largest in the spread-initiating portion and gradually decreases toward the spread terminating portion tapering like a wedge (See FIG. 3). The blood cells are deformed and become unsuited for dyeing in the former (thick) portion and are too scanty in distribution density in the latter (thin) portion, both of which are useless or valueless as data for the medical diagnoses. Such a tendency has heretofore limited the use of such smears, in microscopic examination as diagnostic data, only to the central portion thereof having a suitable thickness. In actuality, the distribution by type of blood cells in a smear is not uniform. Using only a portion of such a smear, wherein blood cells are locally or non-uniformly distributed, as a sample for microscopic examination is not good for medical diagnoses, being liable to lead to an erroneous judgement. It has, furthermore, become evident that such a non-uniformly distributed smear is unsuitable for examination employing an automatic cell discriminating instrument which is connected with an electronic computer. It often makes the examination itself unfeasible.

As a second known method, a mechanical spreading of subject blood employing a mechanical system in place of the above-mentioned manual spreading can be cited, in which the spreader is moved by a mechanical device, not by a human hand. This method has only changed the means of moving the spreader from manual to mechanical, leaving the spreading function itself utterly unchanged or unimproved. It is far from being free from the conventional disadvantages.

As a third method, a smear spreading by means of only centrifugal force, without depending on a spreader, has been developed. It also tends to render the distribution of blood cells non-uniform owing to the difference of specific gravity in various white corpuscles.

SUMMARY OF THE PRESENT INVENTION

It is therefore a primary object of this invention to eliminate the disadvantages accompanied by the prior art.

It is another object of this invention to provide a method of spreading the subject matter over a slide.

It is still another object of this invention to provide an apparatus making the above-mentioned smear preparing highly effective.

Figure 1:
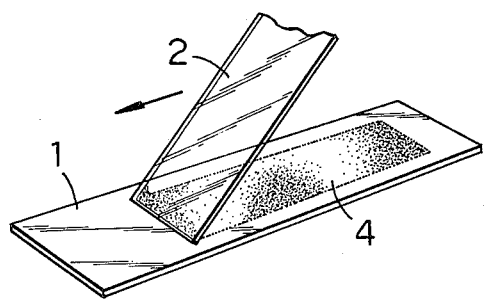
FIG. 1 is a perspective view schematically illustrating the conventional smear spreading method (prior art)
Figure 2:
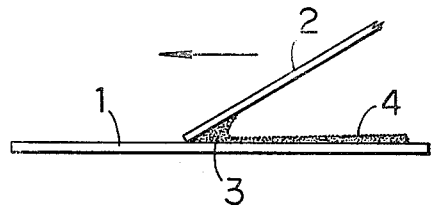
FIG. 2 is a side elevational view schematically illustrating the conventional smear spreading method (prior art)
Figure 3:
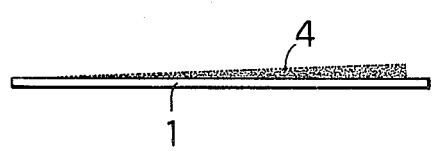
FIG. 3 is a side elevational view of a smear spread over a slide schematically shown (prior art)
Figure 4:
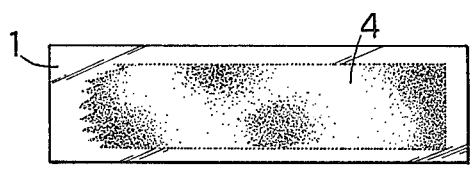
FIG. 4 is a plan view of a smear spread over a slide schematically shown (prior art)
Figure 7:
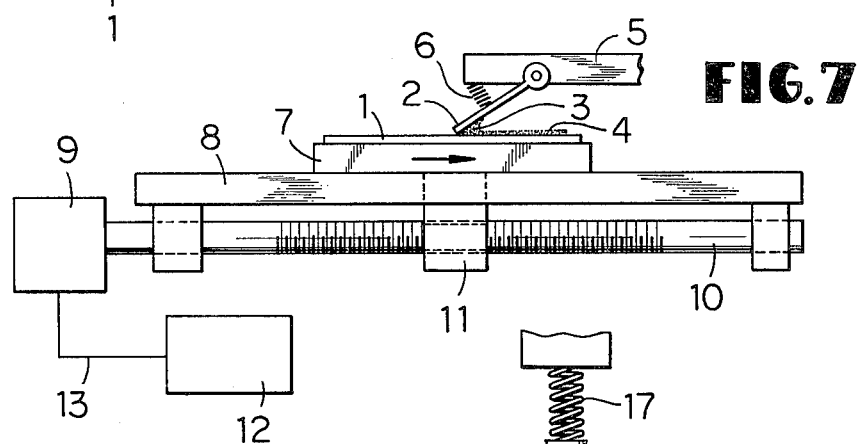
Figure 6:
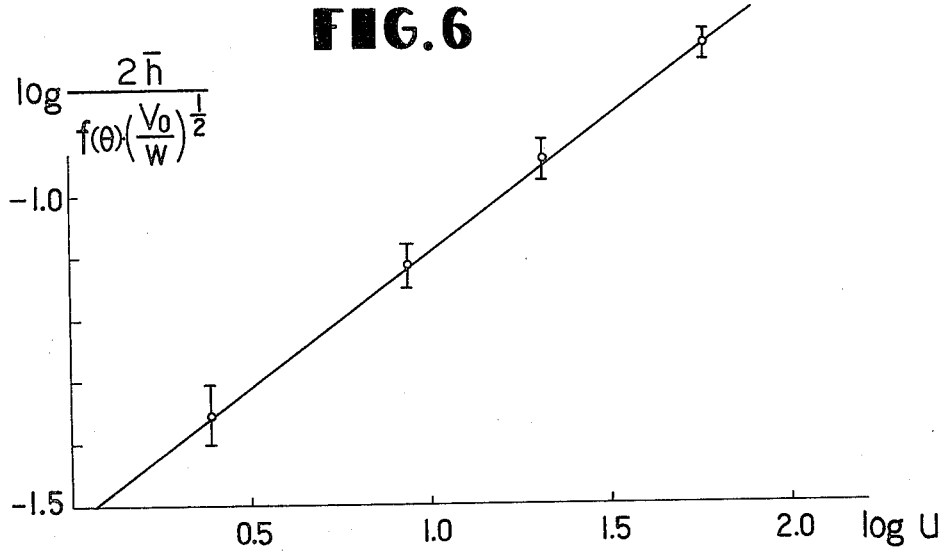

i.e, the correctness of the equation (c) in the under-mentioned description;

FIG. 6 is also a graph showing experimental data for proving the fact that $$\log \frac{2\bar{h}}{f(\theta)\sqrt{\frac{V_O}{w}}}$$

and log u are in a linear functional relation, i.e., the correctness of the equation (d) in the description;

FIG. 7 is an elevational view of an embodiment of this invention, schematically illustrating an apparatus for spreading the subject blood, wherein the spreading speed is continuously varied;

FIG. 7' is a modification of the embodiment in FIG. 7; and

Figure 8:
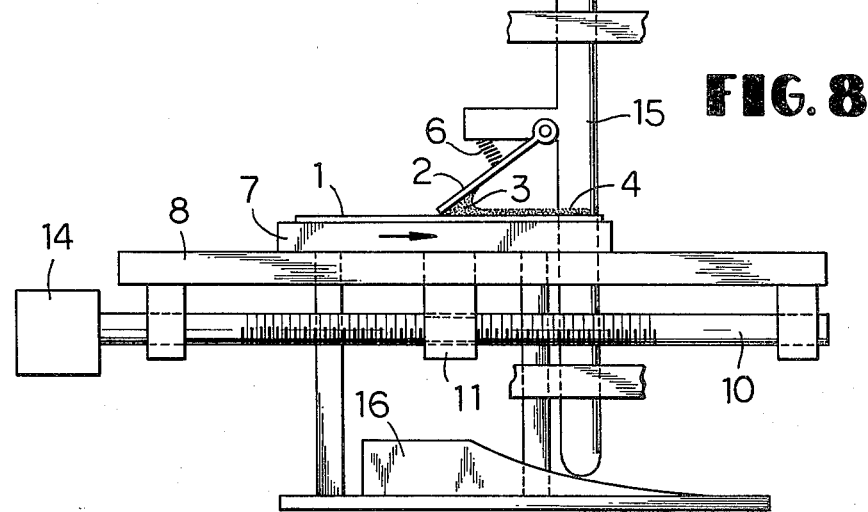
Figure 7:
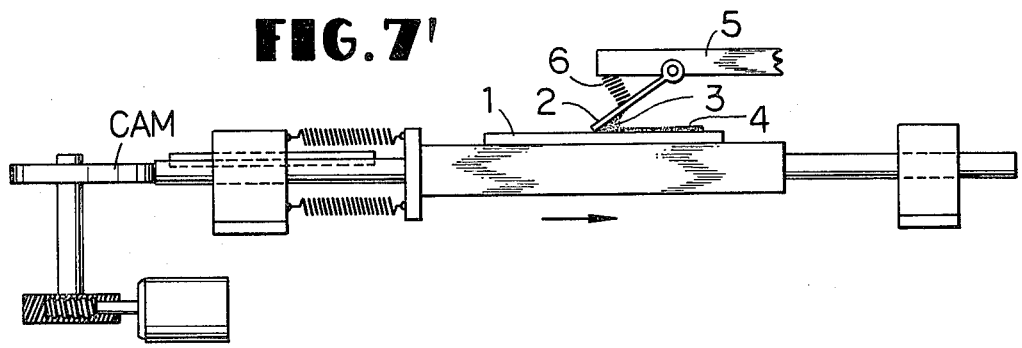

FIG. 8 is an elevational view of another embodiment of this invention, schematically illustrating an apparatus for spreading the subject blood, wherein the angle between the slide and the spreader is continuously varied.

DETAILED DESCRIPTION OF PREFERRED EMBODIMENTS

Figure 5:
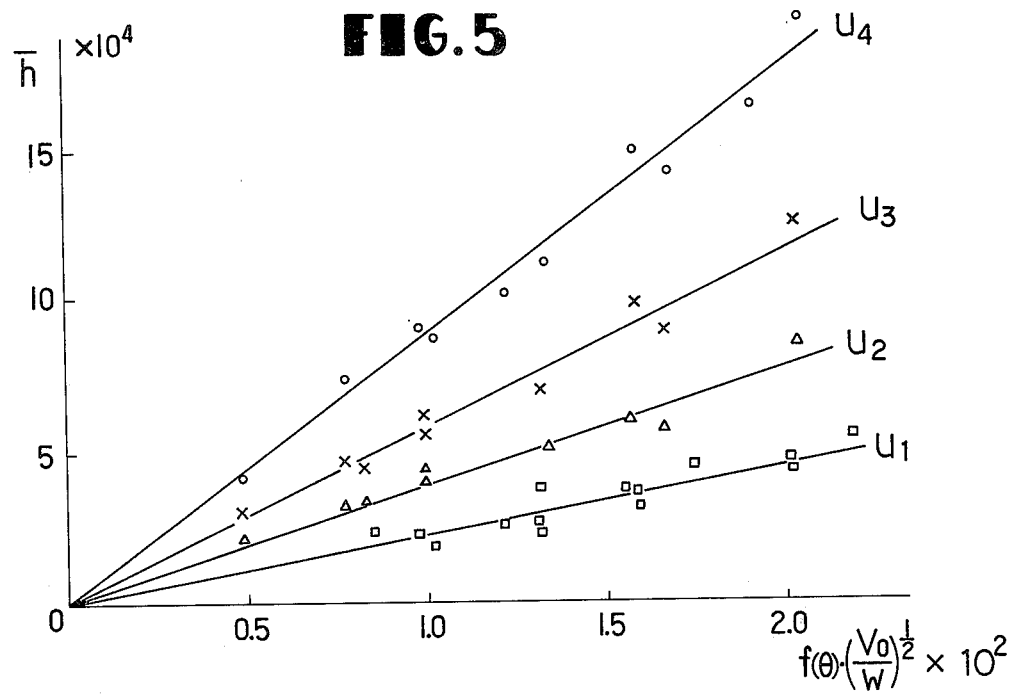
FIG. 5 is a graph showing experimental data for proving the proportional relation between the $\bar{h}$ and $$f(\theta)\sqrt{\frac{V_O}{w}},$$

For better understanding, the principle of this invention will firstly be developed. There has been no precise study physically observing various changes which take place within blood when it is spread over a slide into a filmy smear in accordance with the conventional constant speed spreading methods. Nothing is therefore known regarding the relationships among the thickness of the smear and other essential conditions of the spreading operation: for example, the angle formed between the slide and the spreader (hereinafter simply called spreading angle); the relative moving speed of the spreader against the slide (hereinafter simply called spreading speed); and the residual volume of the subject blood retained or inscribed in the wedge-shaped space between the spreader and the slide (hereinafter simply called blood amount). A series of experiments on this problem to have now have been conducted and there has been discovered the existence of a relationship among the above-mentioned conditions, which can be represented by the following formula or equation:

$$h = C f(\theta) \sqrt{\frac{V}{w}} u^n \quad (a)$$

wherein h is a thickness of the smear measured at an arbitrary point of smear spread, when the blood amount (the volume of blood retained in the wedge shaped space) is V, the spreading angle is $\theta$, and the spreading speed is u. C and n are respectively constants which are determined by the experimental conditions such as qualitative characteristics of the subject blood, w is the width of the smear perpendicular to the spreading direction, which is constant since is equals the width of the spreader, and f($\theta$) is a function of $\theta$ which is provided by the following equation:

$$f(\theta) = \frac{1}{\sqrt{\cot\frac{\theta}{2} - \frac{\pi}{2}\left(1 - \frac{\theta}{180}\right)}} \left\{ \frac{\sqrt{1 + \cot\frac{\theta}{2}\cot\frac{\theta - \Delta}{2}} - 1}{\cot\frac{\theta - \Delta}{2}} \right\}^2 \quad (b)$$

wherein $\Delta$ represents an experimentally determined parameter which has the meaning such that a filmy layer portion contacting the inner side of the spreader of the subject blood retained between the slide and the spreader has been proven of little influence to the process of smear formation through a series of experiments. The angle portion occupied by this filmy layer is denoted by $\Delta$. This angle $\Delta$ can, therefore, be said to be substantially a constant determined by the experimental conditions, being unrelated to V, $\theta$, and u. That the two equations (a) and (b) both almost exactly represent the actual relationship have now been confirmed through constant-speed smearing experiments. Many smear samples were prepared, continuously varying the value of V, $\theta$, and u in various ways, for getting an average film thickness $\bar{h}$, which is calculated by averaging of the thickness ranging from the spread initiating end to the spread terminating end, being represented as the following formula by the induction of the formula (a):

$$\bar{h} = \frac{1}{2} C f(\theta) \sqrt{\frac{V_O}{w}} u^n \quad (c)$$

wherein $V_O$ is the initial blood amount. FIG. 5 represents the interrelation of $\bar{h}$ and $$f(\theta)\sqrt{\frac{V_O}{w}},$$

which has been determined by the above-mentioned experiments. Both are evidently in a direct proportion, thus endorsing the correctness of the equation (c). By means of transforming the equation (c), a following equation (d) can be obtained:

$$\log \frac{2\bar{h}}{f(\theta)\sqrt{\frac{V_O}{w}}} = \log C + n \log u \quad (d)$$

FIG. 6 represents relationship between $$\log \frac{2\bar{h}}{f(\theta)\sqrt{\frac{V_O}{w}}}$$

and log u, that is to say, both are in a linear functional relation, wherein the inclination n and the intersept log C being always constant, which endorses the correctness of the equation (d). From the experimental data the value of the constants can be derived as follows:

c=0.03
and
n=0.44.

On the other hand, determining the value of the constant $\Delta$ by calculation is too complicated and of little value. As the result of a series of actual trials conducted by applying various values to $\Delta$, it has been determined that 4 degrees is best. These constants can be varied, of course, by the experimental conditions such as ambient temperature, characteristic of the glass surface, qualitative characteristic of the subject blood (viscoelasticity or content of surface active substance). However, it can be substantially deemed as constant, so long as the spreading is carried out under a certain fixed condition.

A phenomenon of gradual decreasing of blood film thickness h, while being spread over a slide which everybody experiences in a conventional constant-speed smear preparing, can be explained based on the equation (a). The reason why the thickness h is largest in the initial stage of spreading, incessantly decreasing as the spread goes on, will be evident by noting that the right side value of the equation (a) continuously decreases because of the continuous film formation of the subject blood on the slide surface, as the spreader is moved if it be simply assumed that $\theta$ and u be kept constant. The above assumption teaches that any method which will keep the right side value of the equation (a) constant can be an ideal and desirable way of spreading, practicable in the actual smear preparing. This is the very principle of this invention, i.e., the way of retaining the thickness of the smear h constant by means of gradually changing the spreading speed u and/or the spreading angle $\theta$, as the blood amount V continuously decreases. In other words, the gradual decrease of the blood amount V can be favorably compensated by the incessant adjustment of the spreading speed u and/or the spreading angle $\theta$ in order to maintain the thickness of the smear h constant ranging the whole length thereof or at least for the desired length.

As to a concrete method of adjusting the spreading speed u, so as to maintain the value h, constant represented by the equation (a), as the blood amount V gradually decreases, a first embodiment shall be referred to; as to a method of adjusting the spreading angle $\theta$ so as to maintain the h constant alike as the blood amount V gradually decreases, a second embodiment shall be referred to. A third embodiment should be considered to be a combination of both. By the introduction of these novel ways of thinking, the conventional disadvantages have completely been eliminated to pave the way for getting ideal smears quite useful for medical examination through microscopic observation or the like.

Based on the above-mentioned principle, preferred embodiments of this invention will be described in detail.

Assume that an ideal smear film having a desirable or optimum uniform thickness $h_{op}$ has been obtained by the continuous adjustment of the spreading speed u and the spreading angle $\theta$, then the equation (a) can be transformed into:

$$h_{op} = Cf(\theta)\sqrt{\frac{V}{w}}\, u^n \tag{e}$$

Then the decrement rate of the subject blood volume V retained between both glasses, when the film of uniform thickness $h_{op}$ is formed, is to be represented by the following equation:

$$-\frac{dV}{dt} = w \cdot h_{op} \cdot \frac{dx}{dt} = w \cdot h_{op} \cdot u. \tag{f}$$

Applying the equation (a) thereto leads to:

$$-\frac{dV}{dt} = w\left(\frac{h_{op}}{C}\right)^2 \left\{ \frac{2n}{u^{2n+1}} \cdot \frac{1}{\{f(\theta)\}^2} \cdot \frac{du}{dt} + \frac{2}{u^{2n}} \frac{1}{\{f(\theta)\}^3} \frac{df(\theta)}{dt} \right\}. \tag{g}$$

By means of arranging the two equations in equilibration:

$$\frac{n}{u} \cdot \frac{du}{dt} + \frac{1}{f(\theta)} \frac{df(\theta)}{dt} = \frac{C^2}{2h_{op}} \cdot \{f(\theta)\}^2 \cdot u^{2n+1}$$

can be obtained. By further transforming it, the following equation can be derived:

$$n\frac{d\ln u}{dt} + \frac{d\ln f(\theta)}{dt} = \frac{C^2}{2h_{op}} \{f(\theta)\}^2 u^{2n+1} \tag{h}$$

wherein t represents the time elapsing after the beginning of the spread. The equation (h) indicates the general condition(s) required to provide a smear of uniform thickness $h_{op}$ by means of continuous varying of u and $\theta$, in a predetermined manner.

Depending on this general condition three undermentioned ways of attaining the object can be considered. The embodiments therefor will be explained one by one.

A first embodiment is aimed at obtaining a smear having a desired uniform thickness $h_{op}$, by means of fixing $\theta$ ($=\theta_c$) at a certain angle for allowing only the spreading speed u to vary. Substituting $\theta_c$ for $\theta$, equation (h) is transformed into the following form:

$$\frac{d\ln u}{dt} = \frac{C^2\{f(\theta_c)\}^2}{2n\, h_{op}} u^{2n+1}$$

Further, the next equation may be induced therefrom:

$$u = \frac{u_O}{(1 - Bt)^{\frac{1}{2n+1}}} \tag{i}$$

wherein t represents the time elapsing after the beginning of the spread and B is a constant which can be indicated by the following formula:

$$B = \left(1 + \frac{1}{2n}\right) h_{op}\, u_O \frac{w}{V_O}$$

wherein $V_O$ is the initial amount of blood, $u_O$ being the initial spreading speed. The $u_O$ can be indicated, by means of applying the equation (e), as follows:

$$u_O = \left\{ \frac{h_{op}}{C f(\theta_c)\sqrt{\frac{V_O}{w}}} \right\}^{\frac{1}{n}} \tag{j}$$

In this situation w is constant as it is equal to the width of the spreader, $h_{op}$ is constant as it is the target value of the smear thickness, and $V_O$ is also to be constant if only the targeted whole length of the smear can be determined. All the values in the equation (j) will be determined or settled, if only the values $u_O$ and $\theta_c$ can be determined so as to be practically most convenient and satisfactory to the establishment of the same equation. Using the thus determined values of $V_O$, $\theta_c$, and $u_O$, start the spreading; so a smear of desired uniform thickness can be obtained only by continuously varying u, within the condition of the equation (i), according to the lapse of time t. A program of spreading speed required under this condition has thus been obtained. An apparatus for preparing a smear according to this program is shown in FIG. 7, which schematically illustrates the same in elevation.

A drop of subject blood 3 is placed on a slide 1, and in the usual way a spreader 2 is moved toward the blood drop so that it becomes positioned in a wedge-shaped space, formed between the slide 1 and spreader 2 (glass) where it expands in a lateral direction. In accordance with the invention, the spreader 2 is, being retained by a supporter 5 at a certain fixed acute angle $\theta$ with the slide 1 and biased downwardly by a compression spring 6. The slide 1 is placed on a table 7, which is supported on a carrier 8 for being horizontally movable. Due to the operation of a servomotor 9, a lead screw 10, which is threadedly engaged with a tapped portion of a lug 11 depending from the carrier 8, moves the table 7 supported on the carrier 8. The above-mentioned speed program is set in a servoamplifier 12, which controls the servomotor 9 via a lead (wire) 13 connecting the two. The numeral 4 designates a smear spread on the slide 1.

As can be implicitly understood from the above description of the apparatus, a drop of the subject blood 3 is placed on the slide 1 at a place near the rightward end thereof in FIG. 7. The lower end of the spreader 2, at the lower or inner surface thereof, is contacted with the blood 3 by suitably moving the table 7; upon ascertaining the blood 3 being closely contacted, owing to the capillary action, with both the slide 1 and the spreader 2, start the spreading operation by actuating the servomotor 9. The lead screw 10 rotated by the servomotor 9 moves the table 7 via the threaded engagement at the lug 11. The movement of the table 7 in the arrow-marked direction in FIG. 7 (it means the spreader moves away from the enclosed fluid) is regulated in its speed by the servoamplifier 12 via the lead 13 under the command of the speed control program set therein. In this way the table 7 is moved, in compliance with the command of the speed control program, continuously varying its speed; and the thickness of the spread smear 4 is maintained uniform at a desired value ranging the whole length excluding a small portion of initial and terminal sections of the smear. The speed u is preferably increased continuously. The speed control by the servomotor can, of course, be substituted by another well-known method, for example, by means of a cam rotated by a constant speed motor, wherein the table 7 can be moved at a desired regulated speed just like by means of a program, only by suitably shaping the cam contour. In this respect FIG. 7' is to be referred to.

As a second embodiment, a case, wherein u is fixed constant ($=u_c$) and $\theta$ alone is varied for obtaining a smear of desired uniform thickness $h_{op}$, will be described. Substitute u in the equation (h) by the constant $u_c$, then $$\frac{d \ln f(\theta)}{dt} = \frac{C^2 u_c^{2n+1}}{2h_{op}} \{f(\theta)\}^2$$

is induced, and furthermore the next equation may be deployed:

$$f(\theta) = \frac{f(\theta_O)}{\sqrt{1 - Dt}} \quad (k)$$

wherein D is a constant which can be indicated by the following formula:

$$D = h_{op} u_c \frac{w}{V_O}$$

wherein $f(\theta_O)$ is a constant which can be determined by substituting the angle $\theta$ in the equation (b) with the initial spreading angle $\theta_O$, and $V_O$ is the initial amount of blood; $f(\theta_O)$ can be, on the other hand, transformed by applying the equation (e) as follows:

$$f(\theta_O) = \frac{h_{op}}{C\sqrt{\frac{V_O}{w}} u_c^n} \quad (l)$$

Having variously tried the value $f(\theta)$ by giving various value to $\theta$, it was found that $f(\theta)$ is increased with the increase of $\theta$, and is maximized when $\theta$ is in the range of 50° to 60°, but the maximum value is approximately two times the initial value at the most. As can be seen in the above description, the range of adjustment of the angle $\theta$ is relatively small, when the value of $\theta$ is required to be increased, in order to maintain $h_{op}$ constant, as a compensation of the decrease of the blood amount V. It teaches therefore that the spreading angle $\theta_O$ is desired to be as little as possible, so long as the equations (a) and (b) are established. The value of $\theta$, which has been determined upon considering these conditions, will be put in the equation (b) for getting the value of $f(\theta_O)$. Putting the value $f(\theta_O)$ and the target value $h_{op}$ into the equation (1) and giving practically most convenient values to $V_O$ and $u_c$, which are at the same time satisfactory to the same equation, will lead to the determination of all necessary values. By using thus determined $V_O$, $u_c$, and $\theta_O$, start the spread and continuously vary the spreading angle $\theta$, in accordace with the equations (k) and (b) according as the lapse of time t. Then a smear of desired uniform film thickness $h_{op}$ can be obtained; it means a determination of the control program for the spreading angle under this condition.

An embodiment of an apparatus for spreading a smear under the control of thus determined program is shown in FIG. 8, which schematically illustrates the construction, in elevation, thereof. On a slide 1 a drop of subject blood 3 is placed so as to be positioned in a wedge-shaped space, which is formed between the slide 1 and a spreader 2, being pivotally retained by a vertically slidable supporter 15 and downwardly biased by a compression spring 6. The slide 1 is placed on a table 7, which is supported on a carrier 8 for being horizontally movable. Due to the rotation of a constant speed motor 14, a lead screw 10, which is threadedly engaged with a tapped portion of a lug 11 depending from the carrier 8, moves the table 7 supported on the carrier 8 at a constant speed in the arrow-marked direction. The rotation speed of the motor 14 is set such that the moving speed of the table 7 will agree with the above-mentioned $u_c$ speed. A slope-shaped cam 16 is mounted beneath the table 7, fixed thereto via a suitable bracketing member, so as to be movable together therewith; and the lower end of the supporter 15 is abutted on this cam 16. As the cam 16, together with the table 7, rightwardly moves, the supporter 15 will be gradually raised upward, accompanied by the gradual increase of the spreading angle. The shape of the cam 16 is formed such that it allows the spreading angle to take the value of $\theta_O$ at the initial stage and to vary, with the rightward movement of the table 7 at the speed of $u_c$, according to the above-mentioned angle control program. The numeral 17 designates another compression spring for biasing the supporter 15 downwardly; and 4 indicates a smear spread over the slide 1. As for the operation of this apparatus, a drop of the subject blood is placed on the slide 1 at a place near the rightward end thereof in FIG. 8, and the lower end of the spreader 2 at the inner lower surface thereof, is contacted with the blood 3 by suitably moving the table 7. Upon ascertaining the blood 3 being closely contacted, in the wedge-shaped space owing to the capillary action, with both the slide 1 and the spreader 2, and furthermore the initial spreading angle being $\theta_O$, start the spreading operation by driving the motor 14. As the table 7 is moved rightwardly, the spreading angle is increased, with the lapse of the time t, owing to the upward slope of the cam 16, which causes an upward movement of the supporter 15, wherein the variation of the spreading angle agrees with the preset control program. In this way a desired uniform thickness $h_{op}$ of the smear, ranging the whole or length excluding a small portion of initial and terminal sections of the smear, can be attained.

As a third embodiment, a case, wherein both u and $\theta$ are simultaneously varied in order to attain $h_{op}$, that is a method for seeking a desired uniform thickness of the smear will be described. In this instance, u and $\theta$ shall be varied in accordance with the equation (h), which variation may be manifold according to the combination of the two variables u and $\theta$. Taking up one example of those, a case, in which $\theta$ and u are varied under the condition that the following equation can be established, will be stated:

$$\frac{f(\theta)}{f(\theta_O)} = \left(\frac{u}{u_O}\right)^m \quad (m)$$

wherein $\theta_O$ is an initial spreading angle, $u_O$ is an initial spreading speed, and m is an arbitrary constant, whose value is assumed to be:

$$\frac{f(\theta)}{f(\theta_O)} \leq 2$$

This has been based on a consideration that the uppermost increase limit of the value $f(\theta)$, which is caused by the increase of $\theta$, is desirable to be within the double as large as the initial value $f(\theta_O)$. In the equation (m), $\theta_O$ and $u_O$ can be deemed as constant, so the following equation can be derived therefrom:

$$\frac{d \ln f(\theta)}{dt} = m \frac{d \ln u}{dt}$$

This, in cooperation with the equation (h), enables to introduce the following equation:

$$u = \frac{u_O}{(1 - Et)^{\frac{1}{2(m+n)+1}}} \quad (n)$$

wherein E is a constant which can be indicated as follows:

$$E = \left(1 + \frac{1}{2(m+n)}\right) \frac{w}{V_O} h_{op} u_O$$

In this embodiment, too, the initial spreading angle $\theta_O$ is preferable to be, just like in the second embodiment, as little as possible under the condition that both equations (a) and (b) can be established.

Having determined the value $\theta_O$ in this way, substitute it for $\theta_c$ in the equation (j) and substitute the target value of the film thickness for $h_{op}$. Then, putting a suitable value of $V_O$ in the equation (j) will provide the initial spreading speed $u_O$. In this instance the value of $V_O$ shall be, as a matter of course, selected so that both values $u_O$ and $V_O$ may be technically convenient in the practical use.

With thus determined $\theta_O$, $V_O$, and $u_O$, start the spread and continuously vary the value of u, in accordance with the equation (n), and put at the same time the value of u corresponding to the lapse of time t into the equation (m), the result of which will, in cooperation with the equation (b), provide the value of $\theta$ corresponding to the lapse of time t. If $\theta$ is varied according to the lapse of time t, based on the attained value in the above statement, a smear of desired uniform thickness $h_{op}$ is to be obtained. An apparatus therefor can be readily pictured only by combining the above-mentioned two embodiments, the first and the second, the detailed description being omitted.

In conclusion, advantages of this invention will be summarized hereunder. Smears obtained by this invented method employing the invented apparatus are of uniform thickness ranging over the whole length excluding a small portion of the initial and terminal sections of the smear and that very thickness provides the most suitable value for the examination puroses, when observed on a microscope. Comparing this smear with conventional ones, which are non-uniform in thickness according to the position and thereby usable only at a part thereof, the feature of being usable at any part thereof, ranging the whole length excluding a small portion of the initial and terminal sections of the smear, is characteristic in providing highly precise material data for the medical examination. The uniformity of the thickness, as a result of it, brings about uniform distribution of blood cells in the direction of spreading, which uniform diffusion of blood cells or corpuscles also helps to improve the quality of smears as the data for medical diagnoses. When employing an automatic cell discriminating machine incorporating an electronic computer, conventional smear samples of non-uniform thickness are greatly disadvantageous, which complaints have been completely eliminated by this invention. This invention can be said to have obviated the defects inherent to the conventional smear preparing method.

It will be obvious to those skilled in the art that various changes may be made without departing from the scope of the invention and the invention is not to be considered limited to what is shown in the drawings and described in the specification.

What is claimed is:

1. A method of preparing a smear of a nonfree flowing fluid comprising the steps of:
   (1) placing a drop of the fluid on a slide;

(2) contacting the slide with a spreader at an acute angle $\theta$ to define a wedge-shaped space containing said drop;

(3) causing relative motion at a speed u between the slide and the spreader away from the drop in said space;

(4) creating a smear of said drop on said slide of substantially constant and uniform thickness over substantially the entire length of said smear; and (5) holding said constant thickness of said smear over said length by performing at least one of the following steps (5a) and (5b) while performing step (3);

(5a) causing the speed u of said relative motion to increase continuously the entire time while said smear is being created; and (5b) causing said angle $\theta$ to increase continuously the entire time while said smear is being created.

2. A method in accordance with claim 1 wherein the increase in said speed u and/or said angle $\theta$ is controlled such that for every given point during the course of the smearing the values for the angle $\theta$ and the speed u are selected to give a constant desired value for the thickness h of the smear substantially in accordance with the following equation:

$$h = Cf(\theta)\sqrt{\frac{V}{w}}\, u^n$$

wherein C and n are constants determinable by the characteristics of the subject fluid and the experimental conditions, $f(\theta)$ is a function of $\theta$, V is the volume of the subject fluid retained in the wedge-shaped space formed by the spreader and the slide at a given point, and w is the width of the smear perpendicular to the spreading direction.

3. A method in accordance with claim 1 wherein the angle $\theta$ is maintained constant and only the speed u is varied during said moving step (5).

4. A method in accordance with claim 1 wherein the speed u is maintained constant and only the angle $\theta$ is varied during said moving step (5).

5. A method in accordance with claim 1 wherein both the speed u and the angle $\theta$ are varied during said moving step (5).

6. A method in accordance with claim 1 wherein the method is carried out with the spreader maintained stationary and the slide moving in an essentially horizontal direction.

* * * * *